United States Patent [19]

Lau et al.

[11] Patent Number: 4,939,145

[45] Date of Patent: Jul. 3, 1990

[54] PHENOTHIAZONE DERIVATIVES AND ANALOGS

[75] Inventors: Cheuk K. Lau, Pierrefonds; Joshua Rokach, Laval; Christiane Yoakim; Rejean Fortin, both of Montreal; Yvan Guindon, Ile Bizard, all of Canada

[73] Assignee: Merck Frosst Canada, Inc., Kirkland, Canada

[21] Appl. No.: 298,716

[22] Filed: Jan. 19, 1989

Related U.S. Application Data

[60] Division of Ser. No. 3,354, Jan. 14, 1987, Pat. No. 4,859,667, which is a division of Ser. No. 786,257, Oct. 10, 1985, Pat. No. 4,667,032, which is a continuation of Ser. No. 591,134, Mar. 19, 1984, abandoned, which is a continuation-in-part of Ser. No. 559,471, Dec. 12, 1983, abandoned, which is a continuation-in-part of Ser. No. 536,487, Sep. 28, 1983, abandoned, which is a continuation-in-part of Ser. No. 459,924, Jan. 22, 1983, abandoned.

[51] Int. Cl.$^5$ .................... A61K 31/60; A61K 31/54; A61K 31/535; A61K 31/525
[52] U.S. Cl. ................... 514/224.2; 514/161; 514/165; 514/166; 514/183; 514/228.2; 514/229.8; 514/250; 514/404; 514/415; 514/567; 514/568; 514/569
[58] Field of Search .............. 514/161, 165, 166, 183, 514/228.2, 229.8, 250, 404, 415, 567, 568, 569, 224.2; 544/32, 58.4, 102, 334

[56] References Cited

U.S. PATENT DOCUMENTS 2,395,378  2/1946  Miller ................................. 514/161

FOREIGN PATENT DOCUMENTS 0155623  7/1985  European Pat. Off. .
2247871  4/1973  Fed. Rep. of Germany .
176152   4/1970  France .............................. 514/166

OTHER PUBLICATIONS

Chemical Abstracts, vol. 72, No. 13, 3-30-70, p. 406 (Fujisawa).
Chemical Abstracts, vol. 90, No. 9, 2-26-79, p. 133 (Ghizdavu).
Chemical Abstracts, vol. 78, No. 7, 2-19-73, p. 485 (Shvedov).
Chemical Abstracts, vol. 92, No. 15, 4-14-80, p. 12 (Mitchell).
Journal of the Chem. Soc. Perkin Transactionsi, No. 3 (1982) (Gilchrist).
Chemical Abstracts, vol. 99, No. 9, 8-29-83, p. 622 (Raileanu).
Rev. Roum. Chim. 13 833 (1968).
Rev. Roum. Chim 25 691 (1980).
Ann. Chem. 698 186 (1966).
Rev. Roum. Chim. 17 1745 (1972).
Ann. Chem. 715 122 (1968).
Rev. Roum. Chim 13 1241 (1968).
J. Pharm. Sci. 66 1395 (1977).
Ann. Chem. 614 171 (1958).
J. Bio. Chem. 257 1591 (1982).
Prostaglandins 20 627 (1980).
Sircar et al., Biochem. Pharm., 32, No. 1, 170-172, 1983.
Hawkey et al., Prostaglandins Leukotrienes and Medicine, 10, 405-409, 1983.

*Primary Examiner*—Mukund J. Shah
*Assistant Examiner*—E. C. Ward
*Attorney, Agent, or Firm*—Gabriel Lopez; Hesna J. Pfeiffer

[57] ABSTRACT

Phenothiazone derivatives and analogs thereof, pharmaceutical compositions and methods of treatment are disclosed. These compounds are useful as inhibitors of mammalian leukotriene biosynthesis. As such, these compounds are useful therapeutic agents for treating allergic conditions, asthma, cardiovascular disorders and inflammation.

6 Claims, No Drawings

PHENOTHIAZONE DERIVATIVES AND ANALOGS

Division of Ser. No. 003,354, Jan. 14, 1987, U.S. Pat. No. 4,859,667, which is a division of Ser. No. 786,257, Oct. 10, 1985, U.S. Pat. No. 4,667,032, which is a continuation of Ser. No. 591,134, Mar. 19, 1984, abandoned, which is a CIP of Ser. No. 559,471, Dec. 12, 1983, abandoned, which is a CIP of Ser. No. 536,487, Sept. 28, 1983, abandoned, which is a CIP of Ser. No. 459,924, Jan. 12, 1983, abandoned.

U.S. Pat. No. 4,667,032, Lau et al., is incorporated herein by reference in its entirety.

SUMMARY OF THE INVENTION

This invention is directed to pharmaceutical compositions containing a compound of the Formula I:

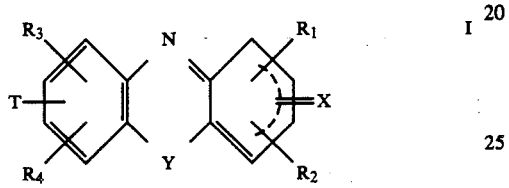

or a pharmaceutically acceptable salt thereof, a method of treatment using said composition and certain novel Formula I compounds.

DETAILED DESCRIPTION OF THE INVENTION

One embodiment of the present invention is a pharmaceutical composition containing a compound of the Formula I:

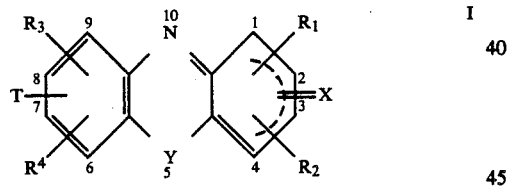

wherein
X is in the 1 or 3 position and is O, S or NR wherein R is H, $C_1$–$C_6$ branched or linear alkyl, CN or phenyl;
Y is O, Se, S, SO, $SO_2$ or NR; and the broken line represents an optional double bond between the 1 and 2 or 2 and 3 position;
$R_1$, $R_2$, $R_3$ and $R_4$ are independently selected from:
(1) hydrogen;
(2) alkyl having 1–6 carbon atoms;
(3) alkenyl having 2–6 carbon atoms;
(4) —$(CH_2)_n$M wherein n is 0–6 and M is
   (a) $OR_5$;
   (b) halogen;
   (c) $CF_3$;
   (d) $SR_5$ wherein $R_5$ is H; lower alkoxy-lower alkyl; lower acyloxy-lower alkyl; $C_1$–$C_6$ alkyl; benzyl; phenyl or substituted phenyl wherein the substituents are $C_1$–$C_3$ alkyl, halogen, CN, $CF_3$, $COOR_6$, $CH_2COOR_6$, $(CH_2)_nNR_8R_9$ wherein n is 0 to 2, $C_1$–$C_3$ alkoxy, OH, halo-$C_1$–$C_6$-alkyl; —$(CH_2)_mCOOR_6$, wherein m is 0 to 6 and $R_6$ is H, phenyl, or $C_1$–$C_6$ alkyl; CN; formyl; perfluoroalkyl; or $CH_2$—$R_{12}$ wherein n is 3 to 4, $R_{12}$ is $C_1$–$C_5$ alkyl, dimethylamino or phenyl;
(e) phenyl or substituted phenyl as defined above for $R_5$;
(f) $COOR_6$;
(g)

wherein $R_{14}$ is H, $(CH_2)_n COOR_6$ wherein n is 0 to 4, $C_1$–$C_6$ alkyl, $CF_3$, phenyl, or substituted phenyl as defined above for $R_5$;
(h) tetrazole;
(i)

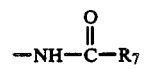

wherein $R_7$ is $C_1$–$C_6$ alkyl, benzyl or phenyl;
(j) —$NR_8R_9$ wherein $R_8$ and $R_9$ are independently selected from H, phenyl or substituted phenyl as defined above for $R_5$, $C_1$–$C_4$ alkyl, $C_1$–$C_4$ alkylaminoalkyl, or may be joined through the N to form a heterocycloalkyl of 5–8 ring atoms;
(k) —$NHSO_2R_{10}$ wherein $R_{10}$ is OH, $C_1$–$C_{16}$ alkyl, $C_1$–$C_6$-alkoxy, phenyl, or $CF_3$;
(l)

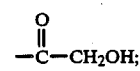

(m) —$SOR_{11}$ wherein $R_{11}$ is $C_1$–$C_6$ alkyl, phenyl or substituted phenyl as defined above for $R_5$, $(CH_2)_mCOOR_6$ wherein m is 1 to 6, CN, formyl or perfluoro-$C_1$–$C_4$ alkyl;
(n) —$CONR_8R_9$;
(o) —$SO_2NR_8R_9$;
(p) —$SO_2R_{13}$ wherein $R_{13}$ is OH, $C_1$–$C_6$ alkyl, H, phenyl or substituted phenyl as defined above for $R_5$, $(CH_2)_mCOOR_6$ wherein m is 1 to 6, CN, formyl or perfluoro-$C_1$–$C_4$ alkyl;
(q) $NO_2$;
(r)

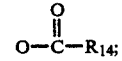

(s)

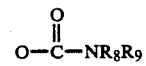

(t)

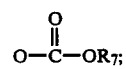

(u) CN;
(v) $NR_{15}R_{16}$ wherein $R_{15}$ and $R_{16}$ are such that $HNR_{15}R_{16}$ is an essential amino acid; or
any two of $R_1$, $R_2$, $R_3$ and $R_4$ are joined (e.g. as —$(CH_2)_{3-4}$—) to add a fourth ring to the three ring structure, said ring having 5 or 6 carbon atoms and being saturated or unsaturated; and, T is H, halogen or CF₃.

The numbers surrounding Formula I designate the substituent positions. T, $R_1$, $R_2$, $R_3$ and $R_4$ may be positioned anywhere in the structure. As an example of compounds with a fourth ring, compounds of Formula II may be prepared by linking two of the substituent groups; $R_1$, $R_2$, $R_3$, $R_4$:

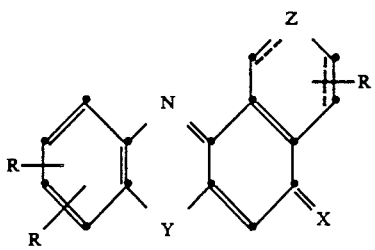

wherein Z may be CH, CH₂ or a bond, the broken lines represent optional double bonds and R represents the substituent groups of Formula I ($R_1$, $R_2$, $R_3$, $R_4$ and/or T) not used to create the fourth ring.

In addition to the compounds of Formula I, the pharmaceutical compositions can also contain other active ingredients, such as cyclooxygenase inhibitors, non-steroidal anti-inflammatory drugs (NSAIDs), peripheral analgesic agents such as zomepirac diflunisal and the like. The weight ratio of the compound of the Formula I to the second active ingredient may be varied and will depend upon the effective does of each ingredient. Generally, an effective does of each will be used. Thus, for example, when a compound of the Formula I is combined with an NSAID the weight ratio of the compound of the Formula I to the NSAID will generally range from about 1000:1 to about 1:1000, and preferably from about 200:1 to about 1:200.

Combinations of a compound of the Formula I and other active ingredients will generally be within the aforementioned broad range and will preferably be within the aforementioned preferred range, but in each case, an effective dose of each active ingredient should be used.

NSAIDs can be characterized into five groups:
(1) the propionic acid derivatives;
(2) the acetic acid derivatives;
(3) the fenamic acid derivatives;
(4) the biphenylcarboxylic acid derivatives; and
(5) the oxicams or a pharmaceutically acceptable salt thereof.

The propionic acid derivatives which may be used comprise: ibuprofen, ibuprufen aluminum, indoprofen, ketoprofen, naproxen, benoxaprofen, flurbiprofen, fenoprofen, fenbufen, ketoprofen, indoprofen, pirprofen, carprofen, oxaprozin, pranoprofen, miroprofen, tioxaprofen, suprofen, alminoprofen, tiaprofenic acid, fluprofen and bucloxic acid. Structurally related propionic acid derivatives having similar analgesic and anti-inflammatory properties are also intended to be included in this group.

Thus, "propionic acid derivatives" as defined herein are non-narcotic analgesics/non-steroidal anti-inflammatory drugs having a free —CH(CH₃)COOH or —CH₂CH₂COOH group (which optionally can be in the form of a pharmaceutically acceptable salt group, e.g., —CH(CH₃)COO⁻Na⁺ or —CH₂CH₂COO⁻Na⁺), typically attached directly or via a carbonyl function to a ring system, preferably to an aromatic ring system.

The acetic acid derivatives which may be used comprise: indomethacin, which is a preferred NSAID, sulindac, tolmetin, zomepirac, diclofenac, fenclofenac, alclofenac, ibufenac, isoxepac, furofenac, tiopinac, zidometacin, acemetacin, fentiazac, clidanac, oxpinac, and fenclozic acid. Structurally related acetic acid derivatives having similar analgesic and anti-inflammatory properties are also intended to be encompassed by this group.

Thus, "acetic acid derivatives" as defined herein are non-narcotic analgesics/non-steroidal anti-inflammatory drugs having a free —CH₂COOH group (which optionally can be in the form of a pharmaceutically acceptable salt group, e.g. —CH₂COO⁻Na⁺), typically attached directly to a ring system, preferably to an aromatic or heteroaromatic ring system.

The fenamic acid derivatives which may be used comprise: mefenamic acid, meclofenamic acid, flufenamic acid, niflumic acid and tolfenamic acid. Structurally related fenamic acid derivatives having similar analgesic and anti-inflammatory properties are also intended to be encompassed by this group.

Thus, "fenamic acid derivatives" as defined herein are non-narcotic analgesics/non-steroidal anti-inflammatory drugs which contain the basic structure:

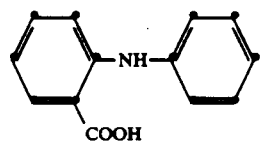

which can bear a variety of substituents and in which the free —COOH group can be in the form of a pharmaceutically acceptable salt group, e.g., —COO⁻Na⁺.

The biphenylcarboxylic acid derivatives which can be used comprise: diflunisal and flufenisal. Structurally related biphenylcarboxylic acid derivatives having similar analgesic and anti-inflammatory properties are also intended to be encompassed by this group.

Thus, "biphenylcarboxylic acid derivatives" as defined herein are non-narcotic analgesics/non-steroidal anti-inflammatory drugs which contain the basic structure:

which can bear a variety of substituents and in which the free —COOH group can be in the form of a pharmaceutically acceptable salt group, e.g., —COO⁻Na⁺.

The oxicams which can be used in the present invention comprise: piroxicam, sudoxicam, isoxicam and 4-hydroxyl-1,2-benzothiazine 1,1-dioxide-4-(N-phenyl)-carboxamide. Structurally related oxicams having similar analgesic and anti-inflammatory properties are also intended to be encompassed by this group.

Thus, "oxicams" as defined herein are non-narcotic analgesics/non-steroidal anti-inflammatory drugs which have the general formula:

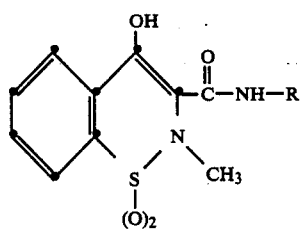

wherein R is an aryl or heteroaryl ring system.

The following NSAIDs may also be used: acemetacin, alminoprofen, amfenac sodium, aminoprofen, anitrazafen, antrafenine, auranofin, bendazac lysinate, benzydamine, beprozin, broperamole, bufezolac, carprofen, cinmetacin, ciproquazone, clidanac, cloximate, dazidamine, deboxamet, d3elmetacin, detomidine, dexindoprofen, diacerein, di-fisalamine, difenpyramide, emorfazone, enfenamic acid, enolicam, epirizole, etersalate, etodolac, etofenamate, fanetizole mesylate, fenclofenac, fenclorac, fendosal, fenflumizole, fentiazac, feprazone, floctafenine, flunixin, flunoxaprofen, fluoproquazone, fopirtoline, fosfosal, furcloprofen, furofenac, glucametacin, guaimesal, ibuproxam, isofezolac, isonixim, isoprofen, isoxepac, isoxicam, lefetamine HCl, leflunomide, lofemizole, lonazolac calcium, lotifazole, loxoprofen, lysin clonixinate, meclofenamate sodium, meseclazone, miroprofen, nabumetone, nictindole, nimesulide, orpanoxin, oxametacin, oxapadol, oxaprozin, perisoxal citrate, pimeprofen, pimetacin, piproxen, pirazolac, pirfenidone, pirprofen, pranoprofen, proglumetacin maleate, proquazone, pyridoxiprofen, sudoxicam, suprofen, talmetacin, talniflumate, tenoxicam, thiazolinobutazone, thielavin B, tiaprofenic acid, tiaramide HCl, tiflamizole, timegadine, tioxaprofen, tolfenamic acid, tolpadol, tryptamid, ufenamate, and zidometacin.

The following NSAIDs, designated by company code number, may also be used:

480156S, AA861, AD1590, AFP802, AFP860, AI77B, AP504AU8001, BPPC, BW540C, CHINOIN 127, CN100, EB382, EL508, F1044, GV3658, ITF182, KCNTE16090, KME4, LA2851, MR714, MR897, MY309, ONO3144, PR823, PV102, PV108, R830, RS2131, SCR152, SH440, SIR133, SPAS510, SQ27239, ST281, SY6001, TA60, TAI-901 TVX2706, U60257, and WY41770.

Finally, NSAIDs which may also be used include the salicylates, specifically aspirin, and the phenylbutazones, and pharmaceutically acceptable salts thereof.

Pharmaceutical compositions comprising the Formula I compounds may also contain inhibitors of the biosynthesis of the leukotrienes such as are disclosed in pending U.S. patent application Ser. Nos. 539,342, filed Oct. 5, 1983, Ser. No. 459,924, filed Jan. 21, 1983, Ser. No. 539,215, filed Oct. 5, 1983, and Ser. No. 547,161, filed Oct. 31, 1983, which are hereby incorporated herein by reference.

The compounds of the Formula I may also be used in combination with leukotriene antagonists such as those disclosed in copending applications U.S. Ser. Nos. 520,051 and 520,052, filed Aug. 5, 1983 which are hereby incorporated herein by reference and others known in the art such as those disclosed in European Patent Application Nos. 56,172 and 61,800; and in U.K. Patent Specification No. 2,058,785, which are hereby incorporated herein by reference.

Pharmaceutical compositions comprising the Formula I compounds may also contain as the second active ingredient, antihistaminic agents such as benadryl, dramamine, histadyl, phenergan and the like. Alternatively, they may include prostaglandin antagonists such as those disclosed in European Patent Application No. 11,067 or thromboxane antagonists such as those disclosed in U.S. Pat. No. 4,237,160. They may also contain histidine decarboxyase inhibitors such as $\alpha$-fluoromethylhistidine, described in U.S. Pat. No. 4,325,961. The compounds of the Formula I may also be advantageously combined with an $H_1$ or $H_2$-receptor antagonist, such as for instance cimetidine, ranitidine, terfenadine, famotidine, aminothiadiazoles disclosed in EP No. 40,696 and like compounds, such as those disclosed in U.S. Pat. Nos. 4,283,408; 4,362,736; and 4,394,508. The pharmaceutical compositions may also contain a $K^+/H^+$ ATPase inhibitor such as omeprazole, disclosed in U.S. Pat. No. 4,255,431, and the like. Each of the references referred to in this paragraph is hereby incorporated herein by reference.

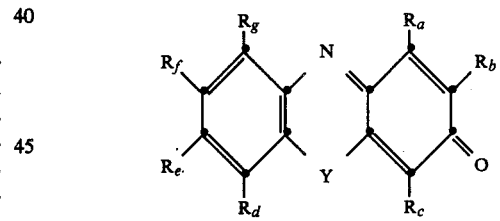

Tables 8 and 9 describe the novel compounds of the present invention:

TABLE 8

NOVEL FORMULA I COMPOUND

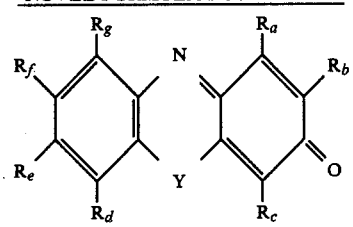

| Y | $R_a$ | $R_b$ | $R_c$ | $R_d$ | $R_e$ | $R_f$ | $R_g$ |
|---|---|---|---|---|---|---|---|
| S | H | H | $CF_3$ | H | H | H | H |
| S | H | $CF_3$ | $CF_3$ | H | H | H | H |
| S | $CF_3$ | H | H | H | H | H | H |

TABLE 8-continued

NOVEL FORMULA I COMPOUND

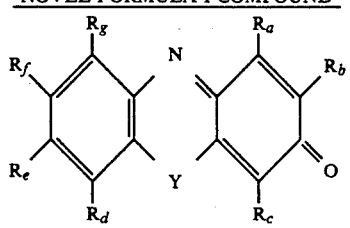

| Y | $R_a$ | $R_b$ | $R_c$ | $R_d$ | $R_e$ | $R_f$ | $R_g$ |
|---|---|---|---|---|---|---|---|
| S | H | F | H | H | H | H | H |
| S | H | SCH$_3$ | H | H | H | H | H |
| S | H | OH | H | H | H | H | H |
| S | H | H | F | H | H | H | H |
| S | H | H | OCH$_3$ | H | H | H | H |
| S | H | H | SCF$_3$ | H | H | H | H |
| S | H | H | CN | H | H | H | H |
| S | H | H | CHO | H | H | H | H |
| S | H | H | COCF$_3$ | H | H | H | H |
| S | H | H | H | H | SCH$_3$ | H | H |
| S | H | H | H | H | OCH$_3$ | H | H |
| S | H | H | H | H | CO$_2$CH$_3$ | H | H |
| S | H | H | H | H | CO$_2$H | H | H |
| S | H | H | H | H | CN | H | H |
| S | H | H | H | H | CHO | H | H |
| S | H | H | H | H | CONH$_2$ | H | H |
| S | H | H | H | H | CH$_2$OH | H | H |
| S | H | H | H | H | CF$_3$ | H | H |
| S | CH$_3$ | H | Cl | H | H | H | H |
| S | H | CH$_3$ | Cl | H | H | H | H |
| S | H | H | Cl | H | F | H | H |
| S | H | Cl | Cl | H | F | H | H |
| S | H | CH$_3$ | H | H | F | H | H |
| S | CH$_3$ | H | H | H | F | H | H |
| S | H | H | Cl | H | OMe | H | H |
| S | H | H | Cl | H | CF$_3$ | H | H |
| S | H | H | Cl | H | CO$_2$Me | H | H |
| S | H | H | Cl | H | CO$_2$H | H | H |
| S | H | H | Cl | H | CN | H | H |
| S | H | H | Cl | H | CHO | H | H |
| S | H | H | Cl | H | CONH$_2$ | H | H |
| S | H | H | Cl | H | CH$_2$OH | H | H |
| S | H | H | OCH$_3$ | H | Cl | H | H |
| S | H | H | CF$_3$ | H | Cl | H | H |
| S | H | OEt | Cl | H | H | H | H |
| S | H | OiPr | H | H | H | H | H |
| S | OMe | H | Cl | H | H | H | H |
| S | OEt | H | Cl | H | H | H | H |
| S | H | OiPr | Cl | H | H | H | H |
| S | H | O-benzyl | Cl | H | H | H | H |
| S | H | OCH$_3$ | Cl | H | H | H | H |
| S | H | OEt | H | H | F | H | H |
| S | H | OEt | H | H | CH$_3$ | H | H |
| S | H | OEt | Cl | H | F | H | H |
| S | H | OEt | Cl | H | CH$_3$ | H | H |
| S | H | H | Cl | H | CH$_3$ | H | H |
| S | H | CH$_3$ | I | H | H | H | H |
| S | H | CH$_3$ | Br | H | H | H | H |
| S | CH$_3$ | H | H | H | CH$_3$ | H | H |
| S | H | CH$_3$ | H | H | CH$_3$ | H | H |
| S | CH$_3$ | H | Cl | H | CH$_3$ | H | H |
| S | H | CH$_3$ | Cl | H | CH$_3$ | H | H |
| S | Cl | H | Cl | H | F | H | H |
| S | H | OMe | Br | H | OMe | H | H |
| S | H | OMe | Cl | H | OMe | H | H |
| S | H | OEt | Br | H | OEt | H | H |
| S | H | OEt | Cl | H | OEt | H | H |
| S | H | OMe | Cl | H | OEt | H | H |
| S | H | OMe | H | H | SMe | H | H |
| O | H | OMe | Br | H | OMe | H | H |
| O | H | OMe | Cl | H | OMe | H | H |
| O | H | H | Cl | H | H | H | H |
| SO$_2$ | H | H | OH | H | H | H | H |
| SO$_2$ | H | OMe | OH | H | OMe | H | H |
| SO$_2$ | OMe | OMe | Me | H | H | H | H |
| SO$_2$ | H | H | OMe | H | H | H | H |
| SO$_2$ | H | OMe | OMe | H | OMe | H | H |
| S | H | H | H | H | H | H | OCH$_3$ |

TABLE 8-continued
NOVEL FORMULA I COMPOUND

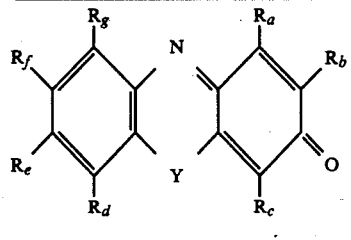

| Y | $R_a$ | $R_b$ | $R_c$ | $R_d$ | $R_e$ | $R_f$ | $R_g$ |
|---|---|---|---|---|---|---|---|
| S | H | $OCH_3$ | H | H | F | H | H |
| S | H | $OCH_3$ | $OCH_3$ | H | H | H | H |
| S | $OCH_3$ | $OCH_3$ | Me | H | H | H | H |
| S | H | H | $COCH_3$ | H | H | H | H |
| S | $OCH_3$ | H | Br | H | $OCH_3$ | H | H |
| S | $OCH_3$ | Cl | Cl | H | $OCH_3$ | H | H |
| S | $OCH_3$ | H | Cl | H | $OCH_3$ | H | H |
| S | H | N(piperazine)N—$CH_3$ | H | H | $OCH_3$ | H | H |
| S | H | N(piperazine)N—$CH_3$ | Br | H | $OCH_3$ | H | H |
| $SO_2$ | H | $OCH_3$ | OH | H | $OCH_3$ | H | H |
| $SO_2$ | NHPr | H | NHPr | H | H | H | H |
| $SO_2$ | N(piperazine)$NCH_3$ | H | N(piperazine)$NCH_3$ | H | H | H | H |
| $SO_2$ | H | $OCH_3$ | N(piperazine)$NCH_3$ | H | $OCH_3$ | H | H |
| $SO_2$ | H | $OCH_3$ | Br | H | $OCH_3$ | H | H |
| S | NHPr | H | NHPr | H | H | H | H |
| S | NHPr | H | NHPr | H | $OCH_3$ | H | H |
| S | H | NHPr | NHPr | H | H | H | H |
| S | H | NHPr | NHPr | H | $OCH_3$ | H | H |
| S | H | $OCH_3$ | $NH_2$ | H | $OCH_3$ | H | H |
| S | H | $OCH_3$ | NHPr | H | $OCH_3$ | H | H |
| $SO_2$ | H | $OCH_3$ | NHPr | H | $OCH_3$ | H | H |
| O | $OCH_3$ | H | Cl | H | $OCH_3$ | H | H |
| O | $OCH_3$ | H | Br | H | $OCH_3$ | H | H |
| O | NHPr | H | NHPr | H | H | H | H |
| $SO_2$ | H | $OCH_3$ | CN | H | $OCH_3$ | H | H |
| $SO_2$ | H | OCH3 | $NHCH_2CO_2R$* | H | $OCH_3$ | H | H |
| $SO_2$ | H | $OCH_3$ | S-n-Bu | H | $OCH_3$ | H | H |
| $SO_2$ | H | $OCH_3$ | $CH_2CO_2R$* | H | $OCH_3$ | H | H |
| $SO_2$ | H | $OCH_3$ | $SO_2CH_3$ | H | $OCH_3$ | H | H |
| S | H | S-n-Bu | H | H | H | H | H |
| S | H | H | S-n-Bu | H | H | H | H |
| S | H | $CH_3$ | S-n-Bu | H | H | H | H |
| S | H | OMe | Br | H | $CF_3$ | H | H |
| S | H | OMe | Br | H | F | H | H |
| S | H | OMe | Br | H | Cl | H | H |
| S | H | OMe | Br | H | Br | H | H |
| S | H | OMe | Br | H | $NMe_2$ | H | H |
| S | H | OMe | Br | H | SMe | H | H |
| S | H | OMe | Br | H | $SO_2Me$ | H | H |
| S | H | OMe | Br | H | Ph | H | H |
| S | H | H | H | Cl | OMe | H | H |
| S | H | OMe | Br | H | Me | H | H |

*R is H or $C_1$-$C_4$ alkyl.

Table 9 describes the novel compounds of the present invention having four rings.

TABLE 9
NOVEL COMPOUNDS OF FORMULA II

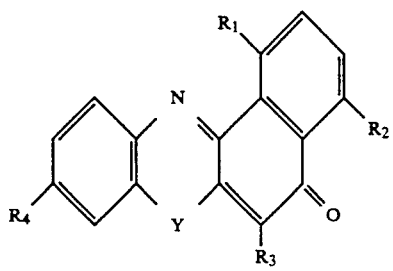

| Y | $R_1$ | $R_2$ | $R_3$ | $R_4$ |
|---|---|---|---|---|
| S | H | H | S-n-$CH_4H_9$ | H |
| S | OH | H | $CH_3$ | H |
| S | $OCH_3$ | H | $CH_3$ | H |
| S | H | H | F | H |
| S | H | H | $CF_3$ | H |
| S | H | H | Cl | $CF_3$ |
| S | H | H | Cl | $SCH_3$ |
| S | H | H | Br | Cl |
| S | H | H | $CH_3$ | Br |
| S | H | H | F | Br |
| S | H | H | $COCH_3$ | Cl |
| S | H | H | $CF_3$ | $CH_3$ |
| S | H | H | S-n-$C_4H_9$ | $CH_3$ |
| S | H | H | $CF_3$ | Cl |
| S | H | H | Cl | *$CH_2COOR$ |
| S | H | H | Cl | *$CH(Me)CO_2R$ |
| S | H | H | Cl | $COCH_3$ |
| S | H | H | H | Cl |
| S | H | H | H | Br |
| S | H | H | H | F |
| S | H | H | H | $CF_3$ |
| S | H | H | H | $CH_3$ |
| S | H | H | H | $CH_2OH$ |
| S | H | H | H | $OCH_3$ |
| S | H | H | H | $SCH_3$ |
| S | H | H | H | *COOR |
| S | H | H | H | *$CH_2CO_2R$ |
| S | H | H | H | *$CH(Me)CO_2R$ |
| $SO_2$ | H | H | NHPr | H |
| $SO_2$ | H | H | N⌒N—$CH_3$ (piperazinyl) | H |
| $SO_2$ | H | H | $NH_2$ | H |
| $SO_2$ | H | H | NHPr | $OCH_3$ |
| S | -1,4-dihydro- | | | H |
| S | H | H | NHPr | $OCH_3$ |
| O | H | H | Cl | H |
| O | H | H | Br | H |
| O | H | H | Br | $OCH_3$ |
| O | H | H | NHPr | $OCH_3$ |

*R is H or $C_1$ to $C_4$ alkyl

Table 10 describes additional novel compounds of the present invention.

TABLE 10
NOVEL COMPOUNDS OF FORMULA I

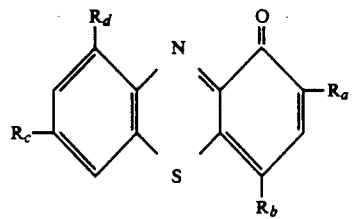

| $R_a$ | $R_b$ | $R_c$ | $R_d$ |
|---|---|---|---|
| t-Bu | t-Bu | H | H |
| t-Bu | t-Bu | F | H |
| t-Bu | t-Bu | Me | H |
| t-Bu | t-Bu | SMe | H |
| t-Bu | t-Bu | H | OMe |

Formula I includes both novel and known compounds. These compounds may be prepared by any process available to the skilled artisan.

One such process for compounds where X=O involves the oxidation of the appropriate phenothiazine as illustrated by the following equations.

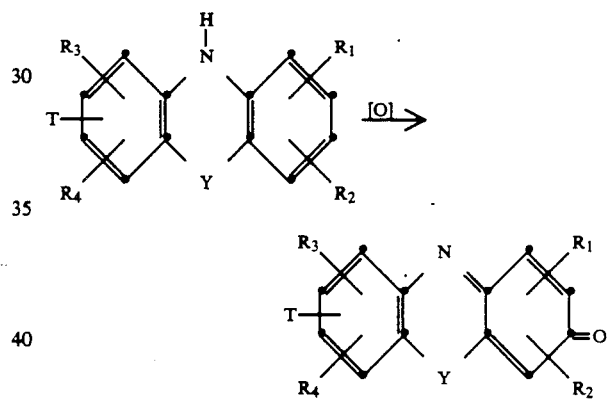

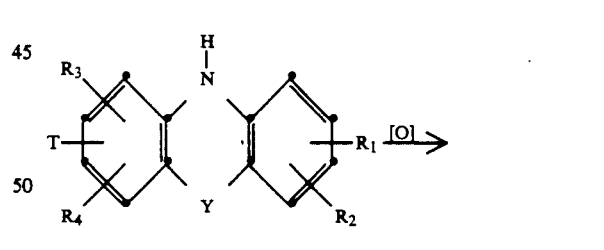

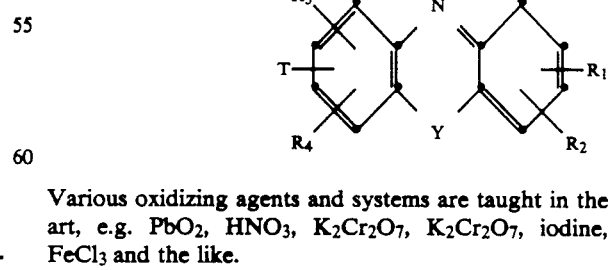

Various oxidizing agents and systems are taught in the art, e.g. $PbO_2$, $HNO_3$, $K_2Cr_2O_7$, $K_2Cr_2O_7$, iodine, $FeCl_3$ and the like.

Another process useful for preparing some Formula I compounds containing halogen substituents is by direct halogenation of an appropriate phenothiazone or analog thereof as illustrated by the following equation.

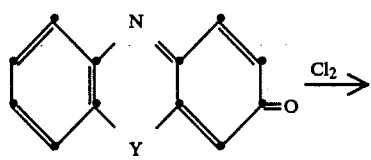

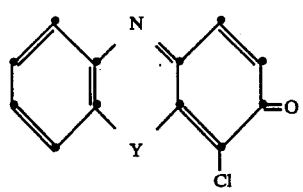

Still another process useful for preparing many of the Formula I compounds is by the reaction of an appropriate aniline with an appropriate quinone as illustrated by the following equation:

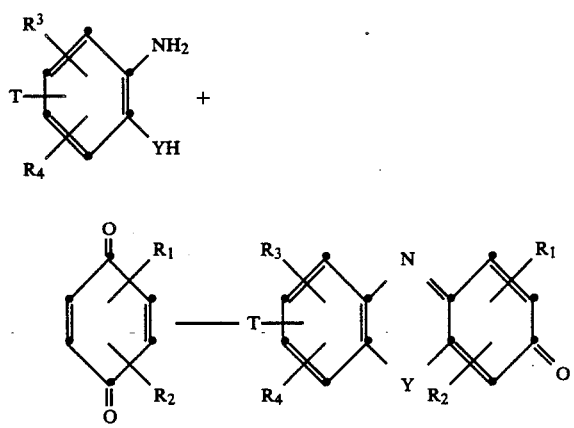

This general process is described in the literature.

A specific process for preparing the intermediate phenothiazin-3-one is illustrated by the following equation:

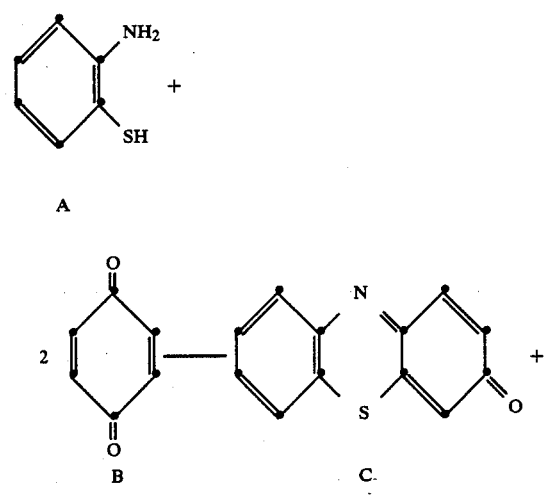

The process requires the use of 2 moles of quinone per mole of aniline. Any suitable solvent may be used. Examples of such solvents are acetic acid, lower alkanols, acetic acid/H$_2$O, loweralkanol/water, other polar solvents and the like. A preferred solvent is one which will dissolve A, B and D and in which C is substantially insoluble. The reaction is readily carried out at room temperature—lower temperatures, e.g. as low as $-10°$ C., may be used—elevated temperatures may also be used but are not required.

What is claimed is:

1. A pharmaceutical composition for inhibiting mammalian leukotriene biosynthesis or action containing a pharmaceutically acceptable carrier and an effective amount of a compound of the Formula I:

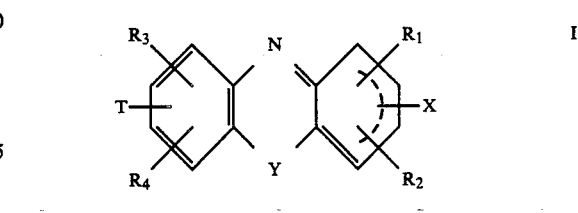

wherein
X is in the 1 or 3 position and is O, S or NR;
R is H, C$_1$-C$_6$ branched or linear alkyl, CN or phenyl;
Y is O, Se, S, SO, SO$_2$ or NR; and the broken line represents an optional double bond between the 1 and 2 or 2 and 3 position;
R$_1$, R$_2$, R$_3$ and R$_4$ are each independently selected from:
 (1) hydrogen,
 (2) alkyl having 1-6 carbon atoms,
 (3) alkenyl having 2-6 carbon atoms,
 (4) —(CH$_2$)$_n$M wherein n is 0-6 and M is
  (a) OR$_5$,
  (b) halogen,
  (c) CF$_3$,
  (d) SR$_5$ wherein R$_5$ is H; lower alkoxyl-loweralkyl; lower acyloxy-loweralkyl; C$_1$-C$_6$ alkyl; benzyl; phenyl or substituted phenyl wherein the substituents are C$_1$-C$_3$ alkyl, halogen, CN, CF$_3$, COOR$_6$, CH$_2$COOR$_6$, (CH$_2$)$_n$NR$_8$R$_9$ wherein n is 0 to 2, C$_1$-C$_3$ alkoxy, OH, halo-C$_1$-C$_6$-alkyl; —(CH$_2$)$_m$COOR$_6$, wherein m is 0 to 6 and R$_6$ is H, phenyl or C$_1$-C$_6$ alkyl; CN, formyl; perfluoralkyl; or CH$_2$—R$_{12}$, wherein R$_{12}$ is C$_1$-C$_5$ alkyl, phenyl or dimethylamino;
  (e) phenyl or substituted phenyl as defined above for R$_5$;
  (f) COOR$_6$;
  (g)

wherein $R_{14}$ is H, $(CH_2)_n COOR_6$ wherein n is 0 to 4, $C_1$-$C_6$ alkyl, $CF_3$, phenyl, or substituted phenyl as defined above for $R_5$;

(h)

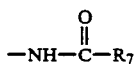

wherein $R_7$ is $C_1$-$C_6$ alkyl benzyl or phenyl;

(i) —$NR_8R_9$ wherein $R_8$ and $R_9$ are independently selected from H, phenyl or substituted phenyl as defined above for $R_5$ or $C_1$-$C_4$ alkyl, $C_1$-$C_4$ alkylamino alkyl, or may be joined through the N to form a heterocycloalkyl of 5-8 ring atoms;

(j) —$NHSO_2R_{10}$ wherein $R_{10}$ is OH, $C_1$-$C_6$ alkyl, $C_1$-$C_6$-alkoxy, phenyl or $CF_3$;

(k)

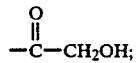

(l) —$SOR_{11}$ wherein $R_{11}$ is $C_1$-$C_6$ alkyl, phenyl or substituted phenyl as defined above for $R_5$, $(CH_2)_m COOR_6$ wherein m is 1 to 6, CN, formyl or perfluoro-$C_1$-$C_4$ alkyl;

(m) —$CONR_8R_9$ (n) —$SO_2NR_8R_9$;

(o) —$SO_2R_{13}$ wherein $R_{13}$ is OH, H, $C_1$-$C_6$-alkyl, phenyl or substituted phenyl as defined above for $R_5$, $(CH_2)_m COOR_6$ wherein m is 1 to 6, CN or perfluoro-$C_1$-$C_4$ alkyl;

(p) $NO_2$;

(r)

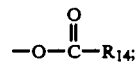

(r)

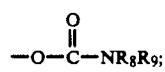

(s)

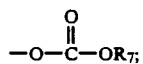

(t) —CN; or any two of $R_1$, $R_2$, $R_3$ and $R_4$ may be joined to form a fourth ring, which may be saturated or unsaturated, of five or six carbons and;

T is H, halogen or $CF_3$.

2. The composition of claim 1 additionally comprising a second active ingredient selected from the group consisting of non-steroidal anti-inflammatory drugs; peripheral analgesic agents; cyclooxygenase inhibitors; leukotriene antagonists; leukotriene inhibitors; $H_2$-receptor antagonists; antihistaminic agents; prostaglandin antagonists; and thromboxane antagonists, wherein the weight ratio of said Formula I compound to said second active ingredient ranges from about 1000:1 to 1:1000.

3. The composition of claim 2, wherein said ratio is about 200:1 to 1:200.

4. The composition of claim 2, wherein the second active ingredient is a non-steroidal anti-inflammatory drug.

5. The composition of claim 3, wherein the non-steroidal anti-inflammatory drug is indomethacin.

6. The composition of claim 1 additionally comprising an effective amount of a second active ingredient selected from the group consisting of non-steroidal anti-inflammatory drugs; peripheral analgesic agents; cyclooxygenase inhibitors; leukotriene antagonists; leukotriene inhibitors; $H_2$-receptor antagonists; antihistaminic agents; prostaglandin antagonists; and thromboxane antagonists.

* * * * *